(12) United States Patent
Hsieh et al.

(10) Patent No.: US 6,810,102 B2
(45) Date of Patent: Oct. 26, 2004

(54) METHODS AND APPARATUS FOR TRUNCATION COMPENSATION

(75) Inventors: Jiang Hsieh, Brookfield, WI (US); Robert H. Armstrong, Waukesha, WI (US); Peter Joseph Arduini, Wauwatosa, WI (US); Robert F. Senzig, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/602,565

(22) Filed: Jun. 24, 2003

(65) Prior Publication Data

US 2004/0066911 A1 Apr. 8, 2004

Related U.S. Application Data

(60) Provisional application No. 60/416,072, filed on Oct. 4, 2002.

(51) Int. Cl.[7] .............................................. A61B 6/02
(52) U.S. Cl. .............................. 378/4; 378/15; 378/901
(58) Field of Search ......................... 378/4, 8, 15, 19, 378/901

(56) References Cited

U.S. PATENT DOCUMENTS

| | | |
|---|---|---|
| 4,136,388 A | 1/1979 | Lindquist |
| 4,189,775 A | 2/1980 | Inouye et al. |
| 4,305,127 A | 12/1981 | Heuscher |
| 4,446,521 A | 5/1984 | Inouye |
| 4,550,371 A | 10/1985 | Glover et al. |
| 4,878,169 A | 10/1989 | Toner et al. |
| 5,043,890 A | 8/1991 | King |
| 5,276,614 A | 1/1994 | Heuscher |
| 5,640,436 A | 6/1997 | Kawai et al. |
| 5,953,388 A | 9/1999 | Walnut et al. |
| 6,307,909 B1 | 10/2001 | Flohr et al. |
| 2004/0066909 A1 * | 4/2004 | Lonn et al. ............... 378/901 |

OTHER PUBLICATIONS

US 5,299,248, 3/1994, Pelc (withdrawn)

* cited by examiner

*Primary Examiner*—David V Bruce
(74) *Attorney, Agent, or Firm*—Carl B. Horton, Esq.; Armstrong Teasdale LLP (57) ABSTRACT

A method includes augmenting partially sampled field of view data using fully sampled field of view data.

45 Claims, 5 Drawing Sheets

Illustration of projecton extension scaled by the expected total attenuation

FIG. 3  Illustration of truncated artifacts

FIG. 4  Total attenuation integrated over all channels as a function of projection angle for a chest phantom FIG. 5    Illustrations of truncation in a clinical setting.

FIG. 6    Illustration of the impact of truncation projection on total attenuation FIG. 7  Illustration of slopes and boundaries estimation FIG. 8  Illustration of fitted water cylinder for truncated projection

FIG. 9  Illustration of projecton extension scaled by the expected total attenuation

METHODS AND APPARATUS FOR TRUNCATION COMPENSATION

CROSS REFERENCE TO RELATED APPLICATIONS

This application claims the benefit of U.S. provisional application No. 60/416,072 filed Oct. 4, 2002.

BACKGROUND OF THE INVENTION

This invention relates generally to methods and apparatus for computed tomographic (CT) image reconstruction, and more particularly to methods and apparatus for a truncation compensation scheme.

Under some scanning conditions, portions of a patient may extend beyond the region measured by a detector, which may lead to image artifacts and an incomplete representation of the imaged object. Some known methods have been published that address the artifact reduction but not the imaging of the portion of the patient that is outside the field of view (FOV). However, it is desirable to image the portion of the patient that extends beyond the FOV.

BRIEF DESCRIPTION OF THE INVENTION

In one aspect, a method is provided. The method includes augmenting partially sampled field of view data using fully sampled field of view data.

In another aspect, an imaging apparatus is provided. The imaging apparatus includes a radiation source, a detector responsive to radiation positioned to receive radiation emitted from the source, and a computer operationally coupled to the radiation source and the detector. The computer is configured to receive data from a Computed Tomography (CT) scan of an object, where the data includes fully sampled field of view data and partially sampled field of view data. The computer is further configured to augment the received partially sampled field of view data using the fully sampled field of view data, and reconstruct an image of the object using the fully sampled field of view data and the augmented partially sampled field of view data.

In a further aspect, a computer readable medium is provided which is encoded with a program configured to instruct a computer to augment partially sampled field of view data, and reconstruct an image using the fully sampled field of view data and the augmented partially sampled field of view data.

DETAILED DESCRIPTION OF THE INVENTION

There is herein provided truncation compensation methods and apparatus for Extended Field-of-View in Computed Tomography Systems. As explained in greater detail below, in one aspect, a method is at least partially based on a property that for parallel sampling geometry, the total amount of attenuation integrated over all channels is independent of the projection angle. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
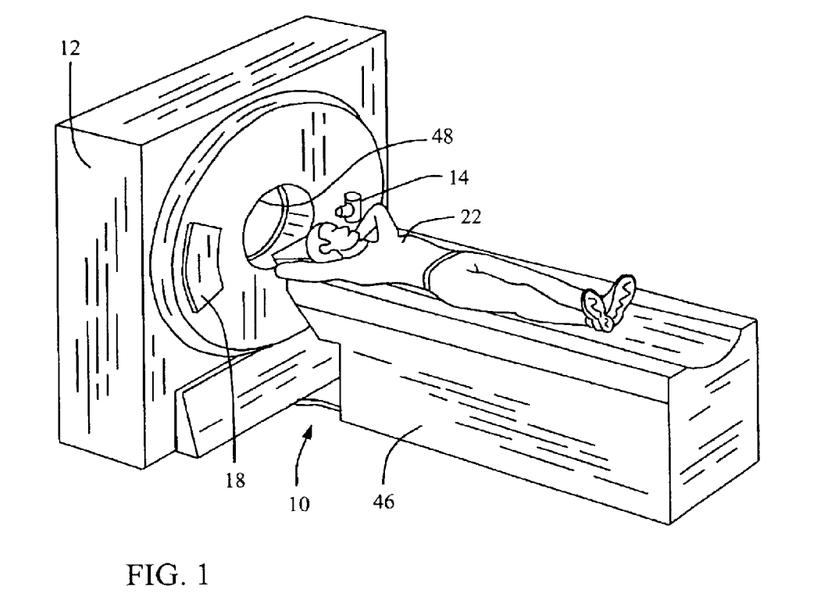
FIG. 1 is a pictorial view of a CT imaging system embodiment.
Figure 2:
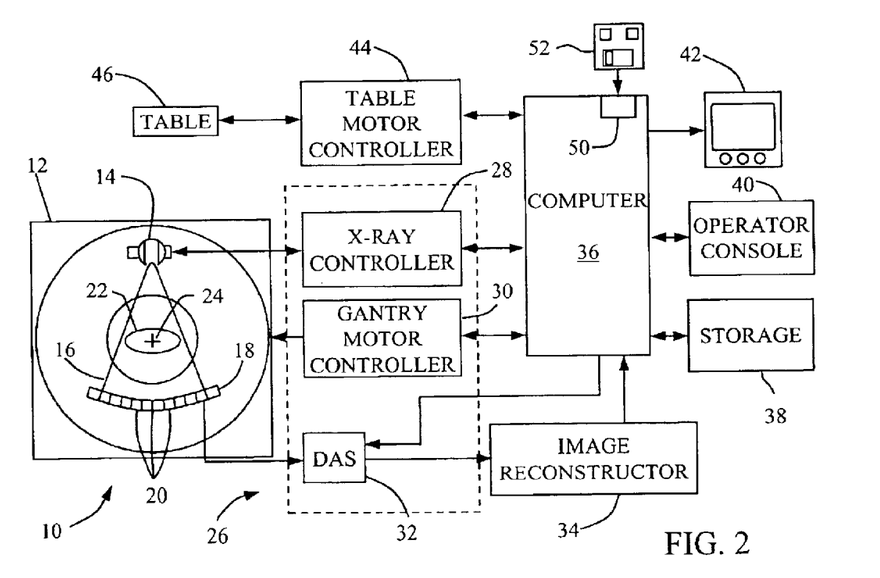
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Under some scanning conditions, portions of patient 22 extend beyond the region measured by detector 18, which may lead to image artifacts and an incomplete representation of the imaged object. The X-ray tube and detector 18 are rigidly held together on a frame which rotates around patient aperture 72. During the course of rotation, measurements are continuously made within a "fully sampled field of view" 60. The attenuation of x-rays traversing any areas of object 22 positioned outside fully sampled field of view 76 is measured at a limited range of rotation angles, and this region is referred to as the "partially sampled field of view" region. In other words, portions that are within fully sampled field of view 76 are positioned within fan 16 such that measurements are obtainable at all gantry angles, and the data collected is defined as fully sampled field of view data. Some portions, however, are within fan 16 at some angles but are outside fan 16 at other angles, and the data collected regarding these portions is defined as partially sampled field of view data.

Figure 3:
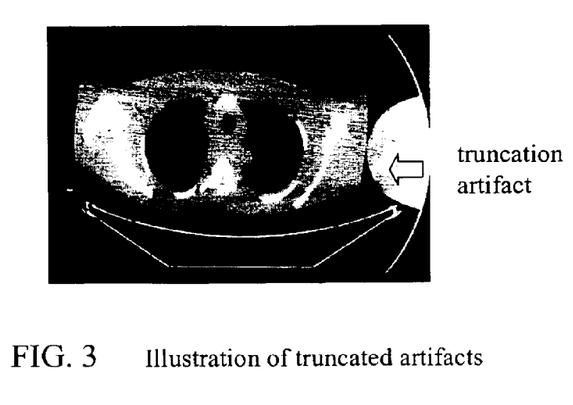
FIG. 3 illustrates truncation artifacts.

Some known methods have been published that address the artifact reduction but not the imaging of the portion of the patient that is outside the field of view (FOV). However, it is desirable to image the portion of the patient that extends beyond the FOV. This is useful in many fields including Oncology, Spin Angiography, Fused imaging systems, and In Economy CT Scanners. The current hardware of known multi-slice CT scanner limits the reconstruction field of view (FOV) to about 50 centimeters (cm.). Although this is sufficient for most clinical applications, it is desirable to expand the FOV to image objects outside this FOV. This may have particular advantages for applications such as oncology or CT/PET. For oncology applications, a larger FOV is desired. This is mainly due to the fact that for radiation treatment planning, the limbs of the patient are often positioned outside the scan FOV for better tumor positioning. The known CT reconstruction algorithms ignore the truncated projections and produce images with severe artifacts. These artifacts may affect an accurate estimation of the attenuation path for treatment planning. One phantom example is shown in FIG. 3. For Fused Imaging systems such as CT/PET (Computed Tomography/Positron Emission Tomography) the FOV of the PET system may not match the existing CT design. It is desirable to have a consistent FOV between the CT and the other imaging system, CT/PET, CT/NUC (CT/Nuclear), or CT/MR (CT/Magnetic Resonence). This correction can be used to adjust the FOV to match. For PET this enables better attenuation correction. Herein described is an algorithmic approach to increase the reconstruction FOV beyond the FOV limited by the detector hardware. This correction algorithm can be applied to various reconstruction algorithms including, but not limited to, Full scan, Halfscan/segment, helical scan, and the cardiac sector based algorithms. Additionally, system 10 is configured to employ the herein described algorithms.

Figure 4:
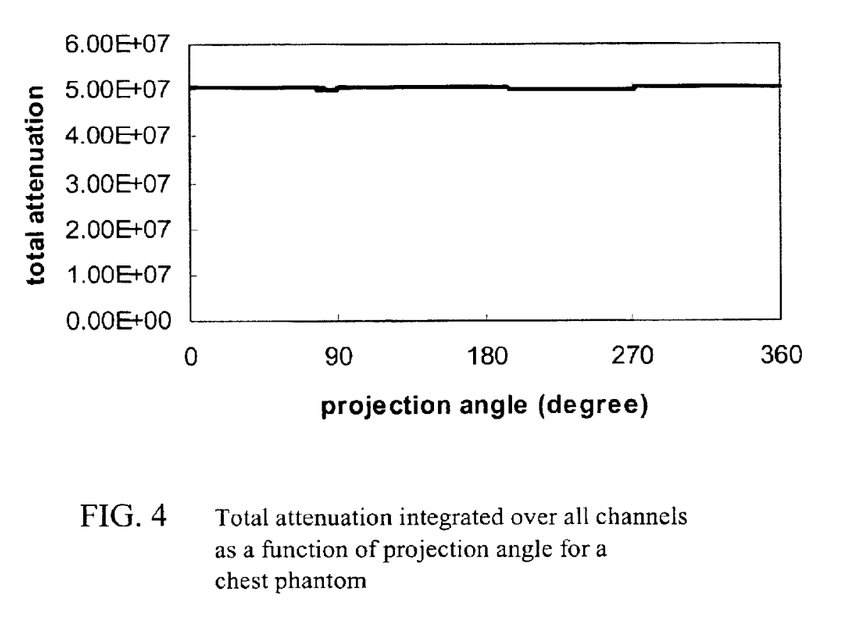
FIG. 4 is a graph showing a total attenuation integrated over all channels as a function of projection angle for a chest phantom.
Figure 5:
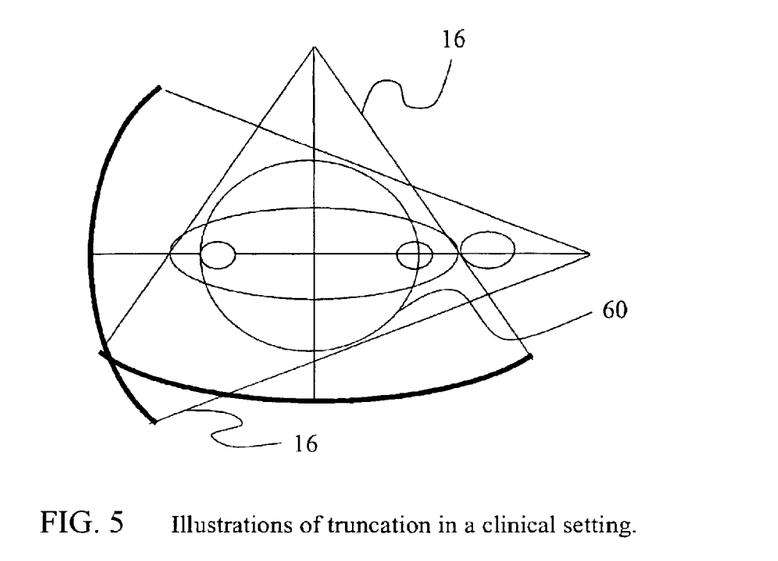
FIG. 5 is an illustration of truncation in a clinical setting.
Figure 6:
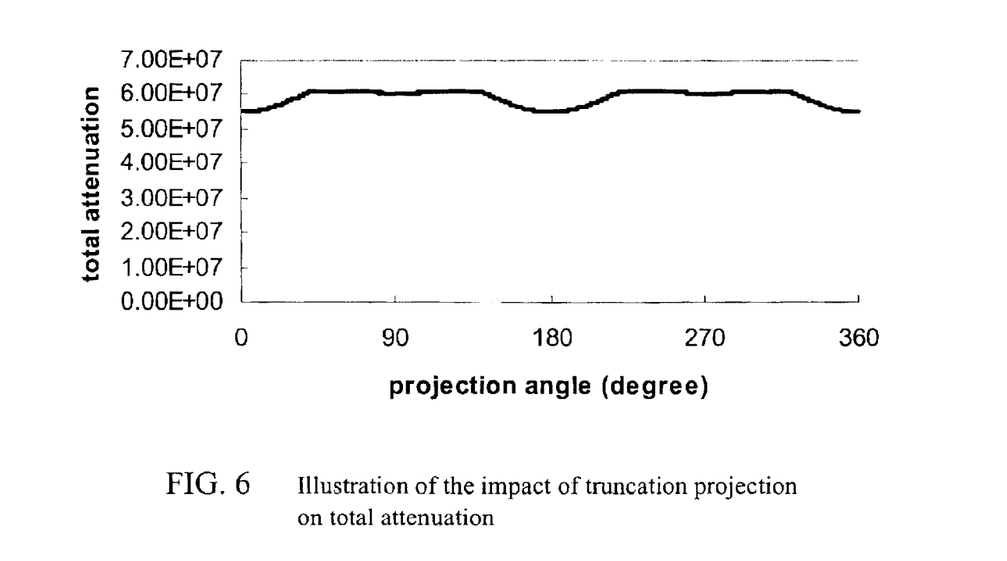
FIG. 6 is a graph illustrating the impact of truncated projection on a total attenuation.
Figure 7:
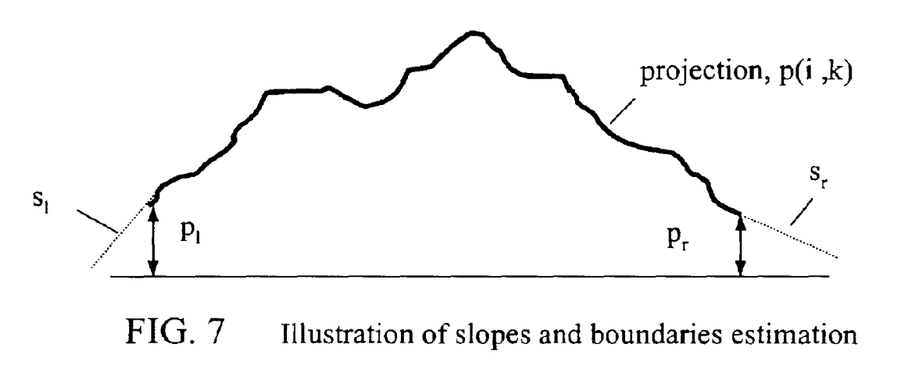
FIG. 7 is an illustration of slopes and boundaries estimation.

FIG. 4 shows the total amount of attenuation plotted as a function of projection angle with a parallel beam sampling geometry for a chest phantom scan. Note that the curve is nearly a horizontal line. This property does not exist, however, for the fan beam sampling geometry. When the scanned object is outside the scan field-of-view (FOV), this property is no longer valid. The amount of deficit is equal to the portion of the object that is outside the projection FOV. In nearly all clinical cases, the projection truncation occurs only in a portion of the projection angles, as illustrated in FIG. 5. In this example, the projection taken at a 3 o'clock position is free of truncation and the projection taken at a 12 o'clock is severely truncated. Therefore, one can rely on the un-truncated projections (i.e., positions around 3 o'clock in FIG. 5, for example) to estimate the amount of truncation for the truncated views (e.g., positions around 12 o'clock for the example in FIG. 5). One early step in the correction process is to perform software fan-beam to parallel-beam rebinning on the pre-processed projections. In one embodiment, that early step is the first step. This process is well known in the art and does not require special data collection. Once the rebinning is completed, the projections are integrated over all detector channels to obtain the total attenuation curve, as shown in FIG. 6. Note that the dips in the total attenuation curve correspond to views with truncation. The flat portion of the curve corresponds to the views in which no object truncation occurs. Once the total amount of the object outside the FOV is estimated, the next step is to estimate the distribution of the missing projection. To achieve this objective, in one embodiment, one first calculates the boundary reading, $p_l$ and $p_r$ as shown below in equation 1, in the truncated projection, as shown in FIG. 7. To reduce noise, in one embodiment, the average of m number of samples is used. m=3 has empirically been shown to be useful in reducing noise. In other embodiments, m is greater than 1 and less than 5.

Equation 1:

$$p_l = \frac{1}{m}\sum_{i=1}^{m} p(i, k) \text{ and } p_r = \frac{1}{m}\sum_{i=1}^{m} p(N - i, k)$$

where N is the number of detector channels, and k is the projection view index. In addition, in one embodiment, the slopes, $s_l$ and $s_r$ near both ends are also estimated. The slope estimation is performed by fitting n samples near the ends with a first order polynomial. n=5 has empirically shown to be useful. In one embodiment, n is greater than 2 and less than 8. In another embodiment, n is greater than 3 and less than 7.

To further improve the reliability of the estimation, projections are used which are acquired from neighboring detector rows. Since human anatomy typically does not change quickly over a small distance (a few millimeters), the boundary samples and the slopes estimated from the neighboring rows do not typically vary significantly. Therefore, the estimated parameters ($p_l$, $p_r$, $s_l$, and $s_r$) can be the weighted average of the values calculated from several detector rows. Based on the boundary and slope information, one estimates a location and the size of a cylindrical water object that can be best fitted to the truncated projection. If we denote the attenuation coefficient of water $\mu_w$, the radius of the cylinder R, and the distance from the cylinder center X, the projection value, p(x), and slope, p'(x), can be described by the following equation.

Equation 2:

$$p(x) = 2\mu_w \sqrt{R^2 - x^2} \text{ and } p'(x) = \frac{-2\mu_w x}{\sqrt{R^2 - x^2}}$$

Since we calculate both p(x) and p'(x) at the truncated projection boundaries, the goal is to estimate R and x so that one obtains the size and location of the cylinder that is to be appended to the missing projection. The formula to estimate these parameters can be described by the following equations:

Equation 3:

$$x_l = \frac{-(s_l)(p_l)}{4\mu_w^2} \text{ and } R_l = \sqrt{\frac{p_l^2}{4\mu_w^2} + x_l^2}$$

Equation 4:

$$x_r = \frac{-(s_r)(p_r)}{4\mu_w^2} \text{ and } R_r = \sqrt{\frac{p_r^2}{4\mu_w^2} + x_r^2}$$

Figure 8:
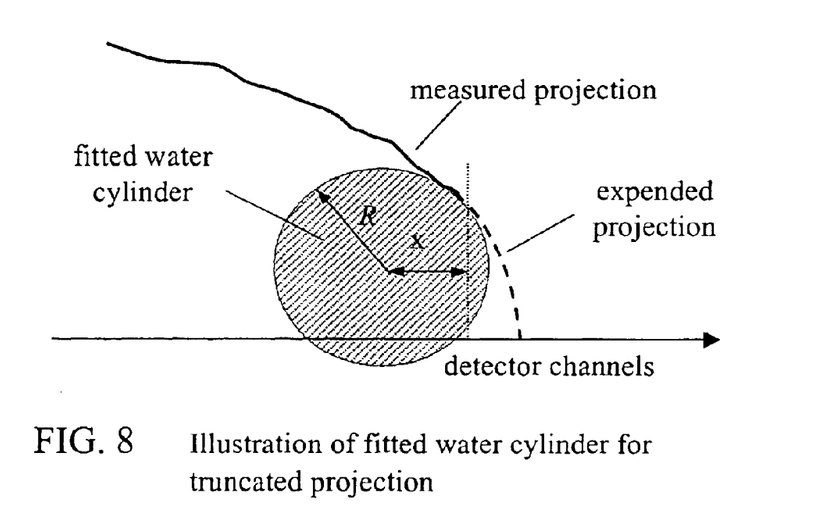
FIG. 8 is an illustration of fitted water cylinder for truncated projection.

The variables represent the estimated location and the size of the cylindrical objects that need to be extended from the truncated object. Once these parameters are determined, the expended projections can be calculated using equation (2). The process is illustrated in FIG. 8.

In this example, a cylindrical water phantom was used for simplicity. In reality, other object shapes, such as an elliptical cylinder, can also be used to increase the flexibility. If a priori information is available on the characteristics of the scanned object, the information can of course be used in the shape and material selection of the appending object. Iterative methods can be used to estimate the missing projection data.

Figure 9:
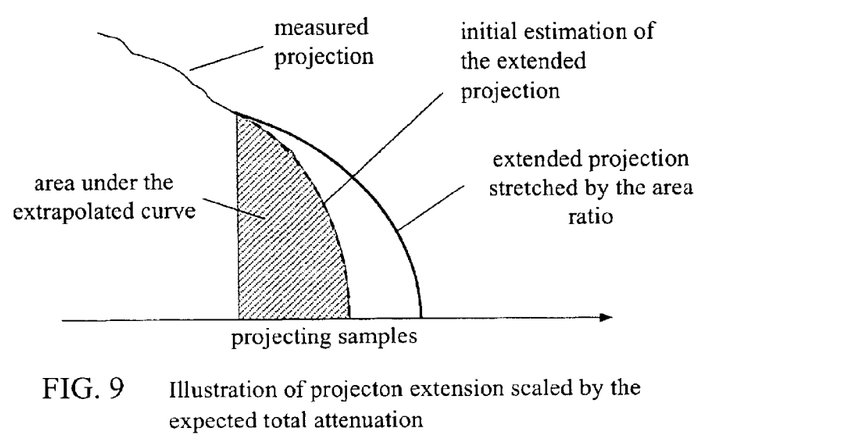
FIG. 9 is an illustration of a projection extension scaled by the expected total attenuation.

The estimated cylinders on both ends of the projection do not always recover the total amount of attenuation for the entire projection, since these objects are determined solely from the slope and boundary samples. None of the information derived from the total attenuation curve (FIG. 6) is used. To ensure proper compensation for the total attenuation loss, the attenuation distribution of the left side, $T_l$, verses the right side, $T_r$, is determined based on the magnitude of $p_l$ and $p_r$.

$$T_l = \frac{p_l T}{p_l + p_r} \text{ and } T_r = \frac{p_r T}{p_l + p_r}$$

where T is the total amount of loss in attenuation determined from FIG. 6. Additionally, if the amount of attenuation under the extended curve is insufficient to make up for the attenuation loss, the estimated projection is stretched to fulfill the attenuation deficits, as illustrated in FIG. 9. On the other hand, if the amount of attenuation under the extended curve exceeds the attenuation loss, the estimated projection is compressed in a similar fashion. In one embodiment, the calculation process is as follows. One first calculates the ratio of the expected total attenuation (shown in Eq. (5)) over the area under the extended projection curve (shown by the shaded region in FIG. 9). If the ratio is larger than unity, the x-axis is scaled by the ratio so that the initial estimated projection (shown by the dotted line in FIG. 9) is further expanded (shown by the solid thick line in FIG. 9). Similarly, if the ratio is significantly smaller than unity, the expanded projection can be compressed in x.

Figure 10:
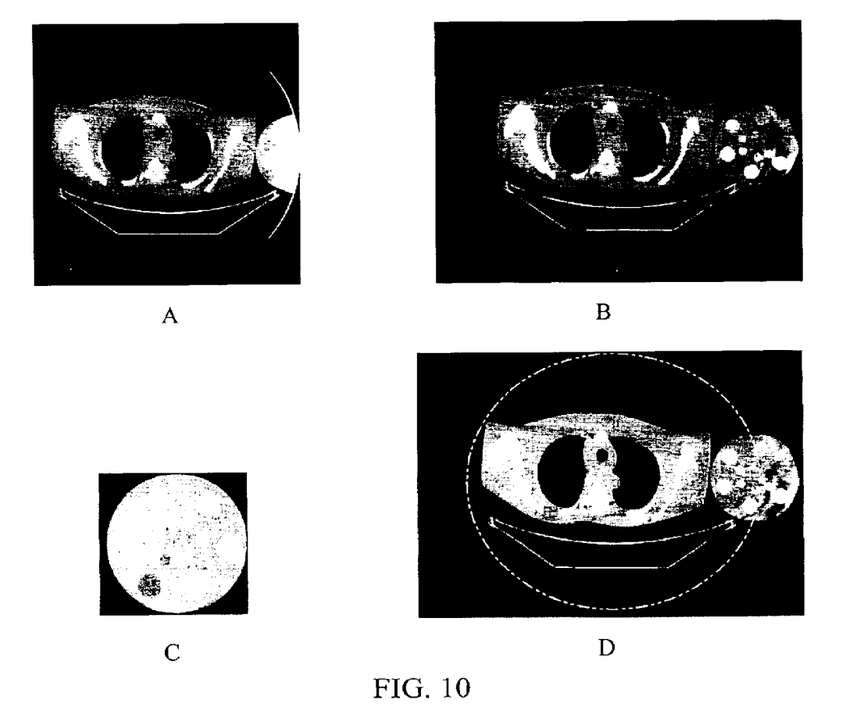
FIG. 10 illustrates a plurality of images.

FIG. 10 shows an example of the reconstructed phantom images without and with correction. A shoulder phantom was scanned in an axial scan mode with a 4×1.25 mm detector configuration. A 15 cm plastic phantom was attached to the shoulder phantom in such a way that the edge of the plastic phantom is near the boundary of the 65 cm FOV. The truncated object is nearly completely recovered. Note that FIG. 10(a) was reconstructed with a 50 cm FOV without truncation correction (current product limit) and FIG. 10(b) was reconstructed with 65 cm FOV with the herein described correction. For reference, the phantom that is partially truncated is in shown in FIG. 10(c).

Although the above described system and methods uses only the conservation of total attenuation, the magnitude, and the slope of the boundary samples to estimate the missing projection distribution, additional information can also be used for the estimation. For example, one could use the Helgason-Ludwig Condition (HL condition) for tomography to further refine the above technique. Additionally, different thresholds can be placed to ensure that the algorithm functions properly under erroneous measurement conditions. For example, one could set the upper and lower limits on the stretch ratio described in FIG. 9 to prevent the condition of increased error due to unreliable measurement. In addition, the slope calculation of $s_l$ and $s_r$ can be set such that it falls within a reasonable range. If the characteristic of the material of the scanned object is known to be significantly different from water, one can also use the attenuation coefficients of the known material (instead of water) to perform size and location calculations shown in Eqs. (3) and (4).

Because the Interpolated data does not have the same image quality as data within the fully sampled FOV it may be useful to tag the image where the FOV becomes extrapolated. In one embodiment, a delineation is provided in a reconstructed image between areas representative of the fully sampled field of view data and the partially sampled field of view data. FIG. 10(d) illustrates the boundary is tagged by a dotted line. This could also be done with a color code or shift in the CT Number. Because the tag may impact the ability to view the image data an easy way is provided to turn on and off the tagging. A user of system 10 is allowed to turn on or off the tagging.

While the invention has been described in terms of various specific embodiments, those skilled in the art will recognize that the invention can be practiced with modification within the spirit and scope of the claims.

What is claimed is:

1. A method comprising augmenting partially sampled field of view data using fully sampled field of view data.

2. A method in accordance with claim 1 wherein said augmenting comprises estimating a distribution of missing projection data.

3. A method in accordance with claim 2 wherein said estimating comprises using projection data acquired from neighboring detector rows.

4. A method in accordance with claim 2 wherein said estimating comprises calculating boundary parameters, $p_l$ and $p_r$, for a truncated projection, in accordance with $$p_l = \frac{1}{m}\sum_{i=1}^{m} p(i, k)$$

and $$p_r = \frac{1}{m}\sum_{i=1}^{m} p(N - i, k),$$

where m is a number of samples used, N is a number of detector channels, and k is a projection view index.

5. A method in accordance with claim 4 wherein m is a number in a range from about 1 to about 5.

6. A method in accordance with claim 2 wherein said estimating further comprises calculating slopes, $s_l$ and $s_r$, by fitting n samples near a plurality of points of truncation with a first order polynomial.

7. A method in accordance with claim 6 wherein n is a number in a range from about 2 to about 8.

8. A method in accordance with claim 6 wherein n is a number in a range from about 3 to about 7.

9. A method in accordance with claim 6 wherein slopes, $s_l$ and $s_r$, are weighted averages of values calculated from a plurality of detector rows.

10. A method in accordance with claim 1 further comprising: scanning an object to obtain fan beam detector data from a plurality of rotation angles around the object; and re-ordering the fan beam detector data into sets of data with parallel sampling paths across the field of view.

11. A method in accordance with claim 10 further comprising summing each parallel path set of data to obtain a path attenuation value for each angle.

12. A method in accordance with claim 11 further comprising estimating a total integral attenuation of the object using a maximum attenuation path.

13. A method in accordance with claim 12 further comprising estimating an amount of truncated integral attenuation in paths with attenuation less than the maximum attenuation path.

14. A method in accordance with claim 13 further comprising calculating a magnitude and a slope at a point of truncation.

15. A method in accordance with claim 14 further comprising estimating a distribution of a truncated projection using the calculated magnitude and slope.

16. A method in accordance with claim 15 wherein said augmenting further comprises augmenting the partially sampled field of view data by adding the estimated distribution to the partially sampled field of view data.

17. A method in accordance with claim 1 further comprising providing a delineation in a reconstructed image between areas representative of the fully sampled field of view data and the partially sampled field of view data.

18. An imaging apparatus comprising:

a radiation source;

a detector responsive to radiation positioned to receive radiation emitted from said source; and a computer operationally coupled to said radiation source and said detector, said computer configured to:

receive data from a CT scan of an object, the data including fully sampled field of view data and partially sampled field of view data;

augment the received partially sampled field of view data using the fully sampled field of view data; and reconstruct an image of the object using the fully sampled field of view data and the augmented partially sampled field of view data.

19. An apparatus in accordance with claim 18 wherein said computer is further configured to estimate a distribution of missing projection data.

20. An apparatus in accordance with claim 19 wherein said computer is further configured to estimate a distribution of missing projection data using projection data acquired from neighboring detector rows.

21. An apparatus in accordance with claim 19 wherein said computer is further configured to calculate boundary parameters, $p_l$ and $p_r$, for the partially sampled field of view data, in accordance with $$p_l = \frac{1}{m}\sum_{i=1}^{m} p(i,k)$$

and $$p_r = \frac{1}{m}\sum_{i=1}^{m} p(N-i,k),$$

where m is a number of samples used, N is a number of detector channels, and k is a projection view index.

22. An apparatus in accordance with claim 19 wherein said computer is further configured to calculate slopes, $s_l$ and $s_r$, by fitting n samples near a plurality of points of truncation with a first order polynomial.

23. An apparatus in accordance with claim 22 wherein said computer is further configured to estimate slopes, $s_l$ and $s_r$, as weighted averages of values calculated from a plurality of detector rows.

24. An apparatus in accordance with claim 18 wherein said computer is further configured to scan an object to obtain fan beam detector data from a plurality of rotation angles around the object; and to re-order the fan beam detector data into sets of data with parallel transmission paths across the field of view.

25. An apparatus in accordance with claim 24 wherein said computer is further configured to sum each parallel path set of data to obtain a path attenuation value for each path.

26. An apparatus in accordance with claim 25 wherein said computer is further configured to estimate a total integral attenuation of the object using a maximum attenuation path.

27. An apparatus in accordance with claim 26 wherein said computer is further configured to estimate an amount of truncated integral attenuation in paths with attenuation less than the maximum attenuation path.

28. An apparatus in accordance with claim 27 wherein said computer is further configured to calculate a magnitude and a slope at a point of truncation.

29. An apparatus in accordance with claim 28 wherein said computer is further configured to estimate a distribution of a truncated projection using the calculated magnitude and slope.

30. An apparatus in accordance with claim 29 wherein said computer is further configured to augment the partially sampled field of view data by adding the estimated distribution to the partially sampled field of view data.

31. An apparatus in accordance with claim 29 wherein said computer is further configured to provide a delineation in a reconstructed image between areas representative of the fully sampled field of view data and the partially sampled field of view data.

32. A computer readable medium encoded with a program configured to instruct a computer to:
augment partially sampled field of view data using fully sampled field of view data; and
reconstruct an image using the fully sampled field of view data and the augmented partially sampled field of view data.

33. A medium in accordance with claim 32 wherein said program is further configured to instruct the computer to estimate a distribution of missing projection data.

34. A medium in accordance with claim 33 wherein said program is further configured to instruct the computer to estimate a distribution of missing projection data using projection data acquired from neighboring detector rows.

35. A medium in accordance with claim 33 wherein said program is further configured to instruct the computer to calculate boundary parameters, $p_l$ and $p_r$, for said partially sampled field of view data, in accordance with $$p_l = \frac{1}{m}\sum_{i=1}^{m} p(i,k)$$

and $$p_r = \frac{1}{m}\sum_{i=1}^{m} p(N-i,k),$$

where m is a number of samples used, N is a number of detector channels, and k is a projection view index.

36. A medium in accordance with claim 33 wherein said program is further configured to instruct the computer to calculate slopes, $s_l$ and $s_r$, by fitting n samples near a plurality of points of truncation with a first order polynomial.

37. A medium in accordance with claim 36 wherein said program is further configured to instruct the computer to estimate slopes, $s_l$ and $s_r$, as weighted averages of values calculated from a plurality of detector rows.

38. A medium in accordance with claim 32 wherein said program is further configured to instruct the computer to scan an object to obtain fan beam detector data from a plurality of rotation angles around the object; and to re-order the fan beam detector data into sets of data with parallel transmission paths across the field of view.

39. A medium in accordance with claim 38 wherein said program is further configured to instruct the computer to sum each parallel path set of data to obtain a path attenuation value for each path.

40. A medium in accordance with claim 39 wherein said program is further configured to instruct the computer to estimate a total integral attenuation of the object using a maximum attenuation path.

41. A medium in accordance with claim 40 wherein said program is further configured to instruct the computer to estimate an amount of truncated integral attenuation in paths with attenuation less than the maximum attenuation path.

42. A medium in accordance with claim 41 wherein said program is further configured to instruct the computer to calculate a magnitude and a slope at a point of truncation.

43. A medium in accordance with claim 42 wherein said program is further configured to instruct the computer to estimate a distribution of a truncated projection using the calculated magnitude and slope.

44. A medium in accordance with claim 43 wherein said program is further configured to instruct the computer to augment the partially sampled field of view data by adding the estimated distribution to the partially sampled field of view data.

45. A medium in accordance with claim 32 wherein said program is further configured to provide a delineation in a reconstructed image between areas representative of the fully sampled field of view data and the partially sampled field of view data.

* * * * *